United States Patent
Ling et al.

(10) Patent No.: US 11,744,683 B2
(45) Date of Patent: Sep. 5, 2023

(54) DENTAL COMPOSITE MILLING BLANKS WITH ENHANCED MECHANICAL PROPERTIES AND METHODS OF MAKING THE SAME

(71) Applicant: James R. Glidewell Dental Ceramics, Inc., Newport Beach, CA (US)

(72) Inventors: Long Ling, Anaheim, CA (US); Yumeng Ma, Irvine, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 383 days.

(21) Appl. No.: 16/904,897

(22) Filed: Jun. 18, 2020

(65) Prior Publication Data

US 2020/0397543 A1    Dec. 24, 2020

Related U.S. Application Data

(60) Provisional application No. 62/925,786, filed on Oct. 25, 2019, provisional application No. 62/863,442, filed on Jun. 19, 2019.

(51) Int. Cl.

| | |
|---|---|
| *A61C 13/00* | (2006.01) |
| *A61K 6/896* | (2020.01) |
| *A61K 6/64* | (2020.01) |
| *C08F 220/32* | (2006.01) |
| *C08F 222/20* | (2006.01) |
| *A61K 6/76* | (2020.01) |
| *C08K 5/14* | (2006.01) |

(52) U.S. Cl.
CPC ............ *A61C 13/0022* (2013.01); *A61K 6/64* (2020.01); *A61K 6/76* (2020.01); *A61K 6/896* (2020.01); *C08F 220/325* (2020.02); *C08F 222/20* (2013.01); *C08K 5/14* (2013.01)

(58) Field of Classification Search
CPC .................................................. A61C 13/0022
See application file for complete search history.

(56) References Cited

U.S. PATENT DOCUMENTS

| | | | |
|---|---|---|---|
| 8,317,516 B2 | 11/2012 | Rusin et al. | |
| 8,507,578 B2 | 8/2013 | Sadoun | |
| 9,962,245 B2 | 5/2018 | Craig et al. | |
| 2015/0182315 A1* | 7/2015 | Okada ................ | A61C 13/0006 264/16 |
| 2018/0228580 A1* | 8/2018 | Oldenburger ............ | C08K 9/06 |

FOREIGN PATENT DOCUMENTS

WO    WO-2017219742 A1 *  12/2017    ......... A61C 13/0004

OTHER PUBLICATIONS

English machine translation of Qui et al. (WO 2017/219742). (Year: 2017).*

* cited by examiner

*Primary Examiner* — Michael F Pepitone
(74) *Attorney, Agent, or Firm* — Charles Fowler

(57) ABSTRACT

A dental resin composite comprising a thermally cured composition of polymeric resin monomers and inorganic fillers that comprise at least 80 wt % total filler loading is provided. Mill blocks made from the dental resin composite and produced via free radical polymerization under high-temperature (approximately 160° C. to 220° C.) and high-pressure process (approximately 300 MPa to 560 MPa) exhibited enhanced mechanical strength and good esthetics suitable for use in CAD/CAM indirect restorations such as, inlays, onlays, crowns and bridges.

15 Claims, No Drawings

DENTAL COMPOSITE MILLING BLANKS WITH ENHANCED MECHANICAL PROPERTIES AND METHODS OF MAKING THE SAME

RELATED APPLICATIONS

This application claims the benefit of, and priority to, U.S. Provisional Patent Application No. 62/863,442, filed Jun. 19, 2019, and U.S. Provisional Patent Application No. 62/925,786, filed Oct. 25, 2019. The entirety of each of the foregoing applications is incorporated herein by reference.

BACKGROUND

The use of computer-aided design and manufacturing (CAD/CAM) in dentistry for indirect dental restorations has been dramatically increased during the last decade. Dental restorations generated by CAD/CAM can meet standardized manufacturing processes with uniform material quality, restoration reproducibility and cost reduction in production. A rising number of machinable esthetic materials have been introduced. Currently, the most popular materials for use in the production of CAD/CAM restorations are glass-ceramics/ceramics. The glass-ceramics/ceramics generally exhibit good mechanical and esthetic properties, but they are brittle and susceptible to failure in the presence of flaws.

Recent developments in resin-based composites have enabled the production of composite blocks suitable for use in some CAD/CAM systems for the fabrication of indirect restorations. Compared to glass-ceramics/ceramics, resin composites are easily fabricated and repaired, and are less susceptible to chipping during the milling procedure. However, resin composite blocks generally have inferior mechanical properties, therefore, a lack of confidence in long-term performance is major obstacle for widespread adoption as longevity and natural esthetics are necessary properties for dental restorations.

Various compositions and processes have been attempted in order to enhance mechanical strength of resin composite blocks without sacrificing good esthetics. For example, U.S. Pat. No. 8,317,516, describes a dental mill blank prepared by mixing a paste including curable resins and fillers derived from a sol-gel process. Furthermore, U.S. Pat. No. 9,962,245, describes a dental mill blank comprising a polymerizable resin having an ethylenically unsaturated group, a thermal initiator having an activation temperature between 100° C. and 150° C., and greater than about 60% by weight of an inorganic filler that has a surface area of at least 65 square meters per gram filler.

U.S. Pat. Pub. No. 2018/0228580 discloses a dental milling blank for the production of permanent indirect restorations via a CAD/CAM process, which comprises 1) inorganic filler with at least 83 wt. % of total mass of the composition; 2) radically polymerizable monomers and 3) one or more initiators for radically curing. The block has a water sorption WSP of less than or equal to 18 µg/mm$^3$ and an E modulus greater than 13 GPa, according to ISO4049 and ADA specification No. 27, respectively.

In addition, U.S. Pat. No. 8,507,578 discloses a method of producing a composite block for dental prosthesis by infiltrating a porous support with a liquid resin and then curing the liquid resin. The volume of liquid resin is at least 2% greater than the volume of the open pores of the support. The support may be a ceramic material, preferably formed from sintering.

U.S. Pat. Pub. No. 2015/0182315 recites a method for producing a dental mill blank, where the polymerizable resin was infiltrated into an inorganic filler molded article or network formed by pressing and cured.

SUMMARY

Dental resin composites, and milling blanks made from the dental resin composites that have enhanced mechanical properties, are provided herein. Methods for fabricating the mill blanks are also provided. Milling blanks made from the dental resin-based composite compositions described herein are suitable for use in making indirect restorations such as inlays, onlays, crowns and bridges using CAD/CAM processes.

Milling blanks described herein having increased mechanical strength without sacrificing good esthetics, are made from compositions of resin monomers and inorganic fillers that are polymerized at a high-temperature and pressure. In one embodiment, a composite composition of resin monomers and fillers comprises 1) an inorganic filler, 2) a polymeric resin monomer with at least two ethylenically unsaturated groups, and 3) a thermal initiator for polymerization. After formulation, the composition is polymerized under high-temperature (e.g., approximately 160° C. to 220° C.) and high-pressure process (e.g., 250 MPa to 560 MPa). In one embodiment, a method of making the milling blanks comprises a hot isostatic pressing (HIP) process.

The resulting resin composite blanks may be in the form of solid milling blocks, including for example, disks, cubes and the like, and near net shape blanks, that are shapeable into single or multi-unit restorations by subtractive manufacturing processes. The polymerized resin composite blanks having significant enhancement of one or more mechanical properties, such as, flexural strength, flexural modulus, fracture toughness, compressive strength, diametral tensile strength and hardness.

DETAILED DESCRIPTION

A method is provided for making a dental resin composite milling blank having significantly enhanced mechanical strength without reducing esthetics qualities. Resin composite mill blanks may be shaped into permanent indirect restorations via computer-aided design and manufacturing (CAD/CAM) processes.

According to one embodiment, a resin-based composition for forming a composite milling blank comprises, i. at least one inorganic filler; ii. a polymerizable resin monomer; iii. a thermal initiator, and iv. optionally, additives. The resin composition is obtained by mixing the inorganic filler and the polymerizable resin monomer, and curing the mixture by way of a high-temperature and high-pressure process.

The composite may be made from one or more polymerizable resin monomers, such as one or more radically polymerizable monomers suitable for use in dental applications. Polymerizable monomers may comprise at least one ethylenically unsaturated group, such as a mono-, di-, or poly-functional (meth)acrylate, which as used herein may include methacrylate or acrylate, or compounds comprising methacrylate or acrylate. A polymerizable resin may comprise bisphenol A glycidyl methacrylate (BisGMA), ethoxylated bis phenol A dimethacrylate (EBPADMA) (having 2 to 30 units of ethoxylation), triethyleneglycol dimethacrylate (TEGDMA), 1,6-hexanediol dimethacrylate (HDDMA), 1,10-decanediol dimethacrylate (D$_3$MA), neopentyl glycol dimethacrylate (NPDMA), polyethylene glycol dimethacrylate, such as poly(ethyleneglycol)(400) dimethacrylate (PEG400DMA) and poly(ethylene glycol)(600) dimethacrylate (PEG600DMA), urethane dimethacrylate (UDMA), trimethylolpropane trimethacrylate (TMPTMA), polytetramethylene glycol dimethacrylate such as polytetramethylene glycol (600) dimethacrylate (PTMDMA), or combinations of one or more polymerizable monomers.

Polymerizable monomers may comprise 10 wt % or more, of the total weight of the polymerizable resin-based composite that includes resin, inorganic filler, initiator and additives. In other embodiments, the polymerizable monomer may comprise from 10 wt % to 25 wt %, such as, from 10 wt % to 23 wt %, 10 wt % to 20 wt %, or 10 wt % to 15 wt %, based on the total weight of the polymerizable resin-based composite. In other embodiments, the polymerizable monomer may comprise from 12 wt % or more, such as from 12 wt % to 25 wt %, or 12 wt % to 20 wt %, based on the total weight of the polymerizable resin-based composite. In other embodiments, the polymerizable monomer may comprise 15 wt % or more, such as from 15 wt % to 25 wt %, 15 wt % to 23 wt % or from 15 wt % to 20 wt %, based on the total weight of the polymerizable resin-based composite material.

In some embodiments, resin monomers comprises EBPADMA having 2 to 6 units of ethoxylation, or EBPADMA having 2 to 4 units of ethoxylation. The resin may comprise a combination of monomers comprising Bis-GMA, UDMA, EBPADMA, and TEGDMA, and in some embodiments, the monomer having the highest weight percent in the monomer combination is EBPADMA. In one embodiment, a ratio of the weight percent of EBPADMA to the weight percent of at least one other polymerizable resin monomer, such as UDMA or BisGMA, may be from 1.5:1 to 5:1, or 1.5:1 to 4:1, or 1.5:1 to 3:1, or 1.5:1 to 2:1, based on the total weight of the polymerizable resin composition. In another embodiment, the weight percent of EBPADMA is greater than or equal to the total weight percent of the remaining polymerizable monomers in the combination.

Inorganic fillers suitable for use in the composite material may be comprised of structural fillers and nanofillers. Structural fillers may be characterized as filler particles having a particle size distribution with a D50 value of approximately 0.1 µm to 2 µm, such as, 0.2 µm to 2 µm, or 0.3 µm to 2 µm, 0.3 µm to 1 µm, 0.1 µm to 0.7 µm, or 0.3 µm to 0.7 µm. Particle size (D50) may be the value of the largest dimension or diameter of particles at 50% of the cumulative distribution. Fillers may include, but are not limited to, conventional glass and/or ceramic dental fillers, such as silica, quartz, barium silicate glass, strontium silicate glass, barium aluminum silicate, fluoroaluminosilicate, strontiumfluoroaluminosilicate, barium boroaluminosilicates and zirconium silicate, and combinations of one or more thereof.

Nanofillers suitable for use herein include fillers having a particle size with a D50 value of less than 200 nm, less than 150 nm, or less than 100 nm, or from 10 nm to 200 nm, or 10 nm to 150 nm, or 10 nm to 100 nm, or 20 nm to 150 nm, or 20 nm to 100 nm. Nanoparticles may include, but are not limited to, an inorganic oxide, such as silica, zirconia or alumnia. Known fillers suitable for use in dental applications, and may include, but are not limited to, colloidal silica such as MT-ST, MT-ST-MS, IPA-ST (Nissan Chemical), fumed (pyrogenic) silica nanoparticle, such as Aerosil OX-50, Aerosil 202, Aerosil R972, or CAB-O-SIL TS-530, or silicate particles including barium silicates and zirconium silicates, for example, Schott Dental Glass Nanofine® NF180 (e.g., GM27884 NF180 and G013-308 particles from Schott). In some embodiments, fillers that provide or increase radiopacity to the composite materials may be added, including ytterbium fluoride and heavy metal oxides, such as barium and zirconium.

Inorganic filler may be added in an amount that provides significantly enhanced mechanical strength to a resin composite milling blank, or in an amount that maximizes strength in the composite blank while maintaining a uniform paste having minimal voids during paste preparation and curing processes. The total filler content may comprise approximately 75 wt % or more, such as from 75 wt % to 90 wt %, 75 wt % to 85 wt %, or 75 wt % to 83 wt %, based on the total mass of the resin-based composition. In other embodiments, the total amount of filler comprises 80 wt % or more, such as from 80 wt % to 90 wt %, 80 wt % to 88 wt %, 80 wt % to 85 wt %, 80 wt % to 83 wt %, or 81 wt % to 88 wt %, 81 wt % to 85 wt %, or 81 wt % to 83 wt %, based on the total weight of the polymerizable resin-based composite. In some embodiments, the D50 value of the structural filler is larger than the D50 value of the nanofiller, and nanofiller may comprise from 1 wt % to 30 wt %, or 1 wt % to 20 wt %, or 1 wt % to 15 wt %, or 1 wt % to 10 wt %, or 5 wt % to 20 wt %, or 5 wt % to 15 wt %, of the total weight of the polymerizable resin-based composite.

To enhance bonding between inorganic filler particles and polymeric resin matrix, thereby obtaining good mechanical properties, the surface of inorganic fillers may be treated with a coupling agent, such as silane, or silane-containing compound, including, for example, γ-methacryloyloxypropyltrimethoxysilane.

Thermal initiators suitable for use herein include organic peroxides and azo compounds, such as dibenzoyl peroxide, cyclohexanone peroxide, dilauroyl peroxide, tert-amyl peroxybenzoate, tert-butyl peroxybenzoate, tert-butylperoxy isopropyl carbonate and di-tert-butyl peroxide, 2,2'-azobisisobutyronitrile, 1,1'-azobis(cyclohaxanecarbonitrile) and 4,4'-azobis(4-cyanovaleric acid), or a combination of one or more thereof. In some embodiments the thermally activated initiator is present in an amount of at least 0.05 wt %, such as from 0.05 wt % to 1 wt %, or from 0.05 wt % to 0.5 wt %, based on the total weight of the polymerizable resin-based composition.

Other additive(s) may be provided that are useful in dental applications and compatible with dental resin composites. Additives may include one or more of, an inhibitor, UV stabilizer, fluorescent and/or opalescent agent(s), colorant or pigment, antimicrobial agents, and the like. For example, a composition may comprise an inhibitor such as 2,6-di-(tert-butyl)-4-methylphenol (BHT) and 4-methoxyphenol (MEHQ); a UV stabilizer such as 2-hydroxy-4-methoxybenzophenone, 2,4-dihydroxy benzophenone; and one or more fluorescent and/or opalescent agent(s) such as, 7-hydroxycoumarin, 7-(2H-naphtho[1,2-d]triazol-2-yl)-3-phenylcoumarin and Lumilux Z-pigments. Other additives that may be suitable for use herein include additives disclosed in U.S. Pat. No. 9,962,245, which is hereby incorporated by reference.

In one embodiment, a polymerizable resin composite material comprises 15 wt % to 25 wt % of at least one polymeric resin monomer comprising an acrylate or methacrylate group, 75 wt % to 85 wt % of at least one inorganic filler, based on the total weight of the composition, and a thermal polymerization initiator to initiate polymerization of the polymeric resin monomer. In this embodiment, the resin monomer comprises EBPADMA. In some embodiments, the resin monomer comprises EBPADMA having 2 to 6 units of ethoxylation, or EBPADMA having 2 to 4 units of ethoxylation, in combination with at least one other polymerizable monomer. In some embodiments, the resin may comprise a combination of monomers that includes BisGMA, UDMA, EBPADMA, and TEGDMA. In other embodiments, the polymerizable composition comprises from 1 wt % to 15 wt % nanofiller having a particle size where D50<100 nm.

In one embodiment, a process for making the composite milling blanks may comprise the steps of making a composite paste comprising polymerizable monomers, inorganic filler, initiator and optionally, additives, and then, thermally polymerizing the resulting paste in a template under high-pressure. The composite paste may be obtained through known composite mixing technology. Inorganic filler and polymeric resin monomer may be mixed in multiple steps to form a uniform paste. A uniformly mixed paste may be filled into a mold of desired shape and size, to form a blank (which, herein, may be used interchangeably with block). Molds may comprise a size and shape suitable for making single unit or multi-unit dental restoration milling blanks. The resulting blank may have a shape such as a solid cube, cylinder, or disk, and the like, or a near net shape having a size and/or shape closer to the final restoration than a known geometry, such as a cube or disk. Molds may be comprised of materials suitable for use in high temperature and/or high pressure molding processes, such as stainless steel, plastic, and the like. Optionally, a pressure pressing technique may be used to apply pressure to densely fill the paste in the desired mold. Methods provided herein may incorporate polymerization steps utilizing higher temperature and/or higher pressure than traditionally used for polymerizing dental methacrylic-based composite materials.

Composite milling blanks may be obtained via thermal polymerization, and a curing process may be carried out under high-temperature and high-pressure. In one embodiment, a curing device designed for thermally polymerizing resin composite material comprises a mold having a cavity (e.g. cubic) with top and bottom openings that is designed for thermally polymerizing the composite material under biaxial pressure to form a polymerized resin composite blank. A thermocouple unit may be provided to control the curing temperature of the device.

In another embodiment, an hot isostatic pressing (HIP) technique may be used to obtain cured blanks by applying pressure and temperature uniformly to all surfaces of the polymerizable resin composite material. HIP processes may be conducted in the presence of an inert gas such as argon. Pressure may be applied during HIP process or under a temperature-controlled device, that is in the range of approximately 200 MPa to 600 MPa, or 250 MPa to 560 MPa, or 250 MPa to 500 MPa, or 250 MPa to 450 MPa, or 250 MPa to 400 MPa, or 275 MPa to 400 MPa, or 300 MPa to 350 MPa. The heating temperature during pressing may be greater than 150° C., or greater than 160° C., including temperatures between 150° C. and 250° C., or 160° C. to 250° C., or 160° C. to 220° C., or 170° C. to 230° C., or 170° C. to 220° C., or 180° C. to 200° C. In some embodiments, thermal polymerization processes may take less than 5 hours, or from approximately 0.5 hour to 3 hours, such as approximately 0.5 hour to 2 hour, or from 1 hour to 2 hours.

In one embodiment, a method for making a polymerized resin composite material is provided that comprises: 1) forming a polymerizable resin composite that comprises 15 wt % to 25 wt % of at least one polymeric resin monomer comprising an acrylate or methacrylate group, 75 wt % to 85 wt % of at least one inorganic filler wherein a portion of the inorganic filler comprises a nanofiller, based on the total weight of the composition, and a thermal polymerization initiator to initiate polymerization of the polymeric resin monomer; 2) placing the polymerizable resin composite in a mold for shaping into a block; and 3) polymerizing the polymerizable resin composite in the mold at a temperature in the range of 160° C. to 220° C. and a pressure in the range of 250 MPa to 560 MPa.

Dental composite milling blanks obtained by methods provided herein may be shaped into a dental restoration by known cutting, milling and polishing process steps. Dental prostheses formed by shaping/milling blanks by the use of CAD/CAM techniques to form indirect restorations, for example, inlays, onlays, veneers, crowns and bridges.

Advantageously, the dental milling blanks prepared by methods described herein comprise significantly higher mechanical strength when compared to corresponding commercially available dental mill block material. For example, in one embodiment, a composite material made according to a method described herein has a flexural strength of at least 240 MPa and flexural modulus in the range of approximately 16 GPa to 19 GPa, which is same or similar to natural dentin (having 16 GPa to 20 GPa), according to testing methods described below. In a further embodiment, a composite material is formed from a polymerizable composition comprising between 80 wt % and 85 wt % filler, wherein polymerized composition has a flexural strength value greater than or equal to 240 MPa and a fracture toughness value greater than or equal to 1.8 ($K_{Ic}$, MPa·m$^{1/2}$).

The advantages of the present invention are further illustrated by the following Examples and Comparative Examples.

Test Methods

Flexural Strength (FS), Flexural Modulus (FM), and Modulus of Resiliency (MR)

For flexural strength (FS), rectangular test samples (thickness×width×length=1 mm×4 mm×12 to 13 mm, n=5) were prepared in accordance with ISO-6872 and tested according to ISO-4049. Flexural modulus (FM) was determined from the slope of the linear region of the stress-strain curve. Modulus of Resiliency (MR) was determined from the area under the elastic portion of the stress-strain curve.

Fracture Toughness (FT)

Fracture toughness (FT, $K_{Ic}$) was determined in accordance with ASTM D 5045-14, by the SENB (single-edge-notched beam) test method. Specimens (thickness×width×length=1.8 mm×3.6 mm×18 mm, n=10) with 1.8 mm central notch were prepared. Actual notch lengths were measured at three points under an optical microscope (≥50×). The specimens were fractured with three-point bending (with a supporting span of 14 mm) at a crosshead speed of 0.5 mm/min on a universal testing machine (Instron 5564). $K_{Ic}$ was calculated from fracture load, notch depth, supporting span and specimen dimensions.

Compressive Strength (CS) and Diametral Tensile Strength (DTS)

For compressive strength (CS) (diameter×height=2×4 mm, n=8) and diametral tensile strength (DTS) (diameter× height=6×3 mm, n=8) test samples were milled from composite block materials on a Glidewell Laboratories TS150™ mill system. Compressive strength (CS) and diametral tensile strength (DTS) were tested according to the ASTM-D695 and ANSI/ADA-Specification #27, respectively. Results for FS, FT, CS and DTS were obtained by testing on an Instron 5564 universal testing machine.

Vickers Hardness

Test samples (n=3) of composite materials having a 5 mm thickness were embedded in acrylic resin mixed with powder, and wet polished sequentially with 80, 500, and 1200 grit SIC, followed by 3 μm-diamond suspension on Grinder-Polisher (EcoMet 300 Pro, Buehler). Vickers Hardness (VH) was then measured for five indentations made on each test sample under a micro Vickers hardness tester (HMV-G, Shimadzu).

EXAMPLES

Abbreviations

BisGMA—bisphenol A glycidyl methacrylate
EBPADMA—ethoxylated bisphenol A dimethacrylate
UDMA—urethane dimethacrylate
TEGDMA—triethyleneglycol dimethacrylate
BPO—dibenzoyl peroxide
BHT—2,6-di-(tert-butyl)-4-methylphenol
UV-9—2-hydroxy-4-methoxybenzophenone
BaG 1 & 2-Sil—barium boroaluminosilicates glass, silanized
Nano silica-Sil—fumed (pyrogenic) silica, silanized
YbF$_3$—ytterbium (III) fluoride HIP—Hot Isostatic Pressing
FS—Flexural Strength (MPa)
FM—Flexural Modulus (GPa)
MR—Modulus of Resiliency (MPa)
FT—Fracture Toughness ($K_{Ic}$, MPa m$^{1/2}$)
CS—Compressive Strength (MPa)
DTS—Diametral Tensile Strength (MPa)
VH—Vickers Hardness (GPa)

Preparation of Composite Pastes:

Composite pastes for Examples 1 through 9 were prepared with components in accordance with Table 1. Homogeneous resin mixtures were made by stirring resin monomers with a thermal initiator and additives until dissolved. The resulting resin mixtures were further mixed with fillers until a uniform paste was formed.

TABLE 1

Resin And Filler Compositions.

| | Component | Ex. 1 | Ex. 2 | Ex. 3 | Ex. 4 | Ex. 5 | Ex. 6 | Ex. 7 | Ex. 8 | Ex. 9 |
|---|---|---|---|---|---|---|---|---|---|---|
| | | Amount (wt. %) | | | | | | | | |
| Resin monomers: | BisGMA | 5.000 | 4.625 | 4.625 | 4.625 | 4.375 | 4.375 | 4.375 | 4.250 | 4.250 |
| | EBPADMA | 10.00 | 10.175 | 10.175 | 10.175 | 9.625 | 9.625 | 9.625 | 9.350 | 9.350 |
| | UDMA | 3.720 | 2.505 | 2.505 | 2.505 | 2.370 | 2.370 | 2.370 | 2.302 | 2.302 |
| | TEGDMA | 1.000 | 0.925 | 0.925 | 0.925 | 0.875 | 0.875 | 0.875 | 0.850 | 0.850 |
| | BPO | 0.1600 | 0.148 | 0.148 | 0.148 | 0.140 | 0.140 | 0.140 | 0.136 | 0.136 |
| | BHT | 0.006 | 0.006 | 0.006 | 0.006 | 0.005 | 0.005 | 0.005 | 0.0051 | 0.0051 |
| | UV-9 | 0.120 | 0.111 | 0.111 | 0.111 | 0.105 | 0.105 | 0.105 | 0.102 | 0.102 |
| | Natural white Z | | 0.006 | 0.006 | 0.006 | 0.005 | 0.005 | 0.005 | 0.0051 | 0.0051 |
| Filler: | BaG-1-Sil | | 30.000 | 30.000 | 30.000 | 30.000 | 30.000 | 30.000 | 30.000 | 30.000 |
| | BaG-2-Sil | 30.000 | 44.500 | 44.500 | 44.500 | 45.500 | 45.500 | 45.500 | 46.000 | 46.000 |
| | BaG-3-Sil | 20.000 | | | | | | | | |
| | ZrG-1-Sil | 10.000 | | | | | | | | |
| | ZrG-2-Sil | 10.000 | | | | | | | | |
| | Nano silica-Sil (D50 = 40 nm) | 5.000 | 2.000 | 2.000 | 2.000 | 2.000 | 2.000 | 2.000 | 2.000 | 2.000 |
| | YbF$_3$ D$_{50}$ = 100 nm) | 5.000 | 5.000 | 5.000 | 5.000 | 5.000 | 5.000 | 5.000 | 5.000 | 5.000 |
| Total: | | 100.000 | 100.000 | 100.000 | 100.000 | 100.000 | 100.000 | 100.000 | 100.000 | 100.000 |
| Curing process | | Press (350 MPa/ 180° C.) | HIP (300 MPa/ 180° C.) | Press (350 MPa/ 180° C.) | HIP (380 MPa/ 180° C.) | Press (350 MPa/ 180° C.) | Press (300 MPa/ 180° C.) | HIP (300 MPa/ 180° C.) | Press (350 MPa/ 180° C.) | HIP (300 MPa/ 180° C.) |

Preparation of Composite Blocks:

Composite pastes of Examples 1 through 9, were filled into cubic molds (14 mm×16 mm×20 mm). Curing processes were completed under temperature and pressure via either a hot isostatic pressing (HIP) in argon, or a thermal curing device using biaxial pressing technique (Press), according to the parameters set forth in Table 1.

The resulting cured composite blocks were evaluated for flexural strength (FS), flexural modulus (FM), modulus of resiliency (MR), compressive strength (CS), diametral tensile strength (DTM), Vickers hardness (VH) and fracture toughness (FT), according to the methods described herein, the results of which were reported in Table 2. Comparative Examples 1 through 5, are commercially available milling block materials, as follows: Grandio blocs (VOCO America, Inc.), Cerasmart® (GC America, Inc.), Lava™ Ultimate (3M, ESPE), Paradigm™ MZ100 (3M, ESPE), Shofu block HC (Shofu Dental Corporation).

TABLE 2

Mechanical Properties Of Composite Materials.

| Ex. # | Filler content (wt %) | FS (MPa) | FM (GPa) | MR (MPa) | CS (MPa) | DTS (MPa) | VH (GPa) | FT ($K_{Ic}$, MPa · $m^{1/2}$) |
|---|---|---|---|---|---|---|---|---|
| Ex. 1 | 80% | 240.1 ± 12.31[b,c,d] | 16.33 ± ± 0.19[d] | 1.77 ± 0.20[c,d] | — | — | — | — |
| Ex. 2 | 81.5% | 245.8 ± 7.7[b,c,d] | 16.20 ± 0.48[d] | 1.87 ± 0.14[b,c,d] | — | — | — | — |
| Ex. 3 | 81.5% | 251.4 ± 11.6[a,b,c] | 15.84 ± 0.42[d,e] | 2.00 ± 0.22[a,b,c] | 583.2 ± 25.7[a] | 68.5 ± 6.4[a,b] | 1.105 ± 0.061[b] | — |
| Ex. 4 | 81.5% | 272.0 ± 23.8[a, b] | 18.50 ± 0.30[b] | 2.01 ± 0.33[a,b,c] | — | — | — | — |
| Ex. 5 | 82.5% | 284.5 ± 8.6[a] | 17.5 ± 0.32[c] | 2.31 ± 0.15[a,b] | 571.0 ± 30.6[a] | 80.6 ± 10.6[a] | — | — |
| Ex. 6 | 82.5% | 253.0 ± 17.1[a,b,c] | 16.19 ± 0.44[d] | 1.99 ± 0.29[a,b,c] | — | — | — | — |
| Ex. 7 | 82.5% | 274.7 ± 16.0[a, b] | 19.54 ± 0.53[a] | 1.94 ± 0.26[a,b,c] | 573.9 ± 44.1[a] | — | 1.174 ± 0.055[a] | 1.96 ± 0.22[a] |
| Ex. 8 | 83% | 250.3 ± 19.3[b,c] | 16.09 ± 0.31[d] | 1.96 ± 0.31[b,c] | — | — | — | — |
| Ex. 9 | 83% | 268.7 ± 9.8[a,b,c] | 17.71 ± (0.47)[b, c] | 2.04 ± 0.15[a,b,c] | — | — | — | — |
| Comp. Ex 1 (Grandio, VOCO) | 86% | 237.4 ± 13.3[c,d] | 15.83 ± 0.54[d,e] | 1.78 ± 0.17[b,c,d] | 497.3 ± 31.8[b] | 67.3 ± 4.3[a, b] | 1.129 ± 0.059[b] | 1.74 ± 0.15[a,b] |
| Comp. Ex. 2 (Cerasmart, GC) | 71% | 212.6 ± 13.8[d,e] | 9.07 ± 0.15[g] | 2.50 ± 0.30[a] | 492.8 ± 39.8[b] | 51.6 ± 13.1[c] | 0.636 ± 0.007[d] | 1.15 ± 0.09[c] |
| Comp. Ex. 3 (Lava Ultimate 3M ESPE)\ | 80% | 198.4 ± 18.5[e,f] | 12.98 ± 0.45[f] | 1.53 ± 0.26[c,d,e] | 433.1 ± 37.6[c] | 69.5 ± 7.1[a,b] | 0.902 ± 0.010[c] | 1.73 ± 0.17[a,b] |
| Comp. Ex. 4 (Paradigm MZ100, 3M ESPE) | 85% | 177.4 ± 14.0[f,g] | 15.01 ± 0.59[e] | 1.05 ± 0.17[e] | 476.9 ± 33.8[b,c] | 62.5 ± 11.2[b,c] | 1.122 ± 0.021[b] | 1.71 ± 0.21[b] |
| Comp. Ex. 5 (Shofu block HC, Shofu) | 61% | 158.3 ± 15.9[g] | 9.38 ± 0.25[g] | 1.35 ± 0.30[d,e] | 427.7 ± 42.8[c] | 52.1 ± 8.3[c] | 0.663 ± 0.018[d] | 1.06 ± 0.09[c] |

Mechanical properties of the resulting polymerized composite blocks and commercially available block materials are reported in Table 2. The data were analyzed by one-way ANOVA and Tukey tests (p≤0.05). Values in the same column with the same superscript (e.g., $^{a, b, c}$ or $^d$) are not statistically different according to the statistical tests used.

Samples made from the composite block materials of Examples 1-9 demonstrated superior mechanical properties compared to other commercial blocks tested. Examples 1-9 demonstrated higher values, or significantly higher values, for flexural strength and flexural modulus than the commercial blocks. Modulus of resilience has similar results as flexural strength and flexural modulus except that Examples 1-2 and 8 demonstrated lower MR values than Comp. Ex. 2, and Example 1 has a similar value as Comp. Ex. 1. Compressive strength (CS) was tested for Examples 3, 5 and 7, which all demonstrated significantly higher CS than Comp. Examples 1 through 5. Examples 3 and 5 were tested for diametral tensile strength, and demonstrated higher values, or significantly higher values, for diametral tensile strength than Comparative Examples 1 through 5. Examples 7 had a significantly higher VH value, and higher FT value, than Comp. Examples 1 through 5, and Examples 3 had the same value as Comp. Examples 1. Advantageously, FM values for Examples 1-9 were same or similar to the reported value of natural dentin (16 GPa to 20 GPa).

We claim:

1. A method of making a polymerized composite block for use in dental restorations, comprising:
   a) providing a polymerizable resin composite that comprises resin components, the resin components comprising:
   i) 15 wt % to 25 wt % of a combination of polymeric resin monomers comprising bisphenol A glycidyl methacrylate (BisGMA), ethoxylated bis phenol A dimethacrylate (EBPADMA), triethyleneglycol dimethacrylate (TEGDMA), and urethane dimethacrylate (UDMA);
   ii) 75 wt % to 85 wt % of at least one inorganic particle filler, based on a total weight of the polymerizable resin composite; and
   iii) a thermal polymerization initiator to initiate polymerization of the combination of polymeric resin monomers;
   b) mixing the resin components to obtain a uniform polymerizable resin composite mixture and placing the uniform polymerizable resin composite mixture in a mold for shaping into a block; and
   c) polymerizing the polymerizable resin composite in the mold at a temperature in a range of 160° C. to 220° C. and a pressure in a range of 250 MPa to 560 MPa.

2. The method of claim 1, wherein the combination of polymerizable resin monomers consists essentially of bisphenol A glycidyl methacrylate (BisGMA), ethoxylated bis phenol A dimethacrylate (EBPADMA), triethyleneglycol dimethacrylate (TEGDMA), and urethane dimethacrylate (UDMA).

3. The method of claim 1, wherein the polymerizable resin composite comprises EBPADMA having 2 to 6 units of ethoxylation.

4. The method of claim 1, wherein the polymerizable resin composite comprises EBPADMA having 2 to 4 units of ethoxylation.

5. The method of claim 1, wherein the polymerizable resin composite comprise 80 wt % to 85 wt % inorganic filler.

6. The method of claim 1, wherein the at least one inorganic particle filler is selected from one or more of or a combination of two or more of silica, quartz, barium silicate glass, strontium silicate glass, barium aluminum silicate, fluoroaluminosilicate, strontiumfluoroaluminosilicate, barium boroaluminosilicates and zirconium silicate.

7. The method of claim 1, wherein the at least one inorganic particle filler comprises a nanofiller having a particle size of less than 100 nm (D50<100 nm) and a structural filler having a D50 value that is greater than the nanofiller.

8. The method of claim 7, wherein the nanofiller comprises 1 wt % to 10 wt % of the polymerizable resin composite.

9. The method of claim 1, wherein the method for polymerizing the polymerizable resin composite comprises a hot isostatic pressing process.

10. The method of claim 1, wherein the thermal polymerization initiator is selected from an organic peroxide compound and an azo compound.

11. A polymerizable resin composite material that is polymerizable into a millable block for use in milling dental restorations, comprising:
 a polymerizable resin composite that comprises:
 i) 15 wt % to 25 wt % of a combination of polymeric resin monomers comprising bisphenol A glycidyl methacrylate (BisGMA), ethoxylated bis phenol A dimethacrylate (EBPADMA), triethyleneglycol dimethacrylate (TEGDMA), and urethane dimethacrylate (UDMA);
 ii) 75 wt % to 85 wt % of at least one inorganic particle filler, based on a total weight of the polymerizable resin composite; and
 iii) a thermal initiator to initiate polymerization of the combination of polymeric resin monomers;
 wherein the polymerizable resin composite material is polymerizable into a block material having a flexural strength greater than or equal to 240 MPa.

12. The polymerizable resin composite material of claim 11, wherein the polymerizable resin composite material is polymerizable into a block material having a flexural modulus greater than 16 GPa and less than 20 GPa.

13. The polymerizable resin composite material of claim 11, wherein the polymerizable resin composite material is polymerizable into a block material having a fracture toughness greater than 1.80 $MPa*m^{1/2}$.

14. The polymerizable resin composite material of claim 11, comprising between 80 wt % and 85 wt % inorganic filler.

15. The polymerizable resin composite material of claim 11, comprising between 1 wt % and 10 wt % of a nanofiller having a D50 value of less than 100 nm.

* * * * *